United States Patent
Shemano

[11] 3,953,602
[45] Apr. 27, 1976

[54] PHARMACEUTICALLY USEFUL OXYGEN CONTAINING HETEROCYCLIC DERIVATIVES

[75] Inventor: Irving Shemano, Cincinnati, Ohio

[73] Assignee: Richardson-Merrell Inc., Wilton, Conn.

[22] Filed: June 15, 1973

[21] Appl. No.: 370,423

[52] U.S. Cl. .............................. 424/283; 424/288
[51] Int. Cl.² .................. A61K 31/35; A61K 31/34
[58] Field of Search ........................... 424/283, 285

*Primary Examiner*—Jerome D. Goldberg
*Attorney, Agent, or Firm*—L. Ruth Hattan; E. O. Retter; G. W. Rauchfuss, Jr.

[57] ABSTRACT

Compounds of the following general formula are useful in the treatment of conditions of delayed hypersensitivity:

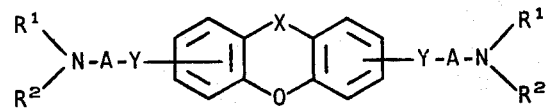

wherein X represents a bond, —CH$_2$—, or carbonyl; Y represents a vinylene group,

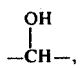

carbonyl, oxygen, divalent sulfur, or carbonyloxy with the proviso that when Y is

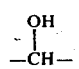

or vinylene, X is not carbonyl; A represents a straight or branched alkylene chain of from 1 to 6 carbon atoms with the proviso that when Y is vinylene, A contains from 1 to 5 carbon atoms and with the proviso that when Y is carbonyloxy or carbonylthio, A contains from 2 to 6 carbon atoms; each of R$^1$ and R$^2$ represents hydrogen, a straight or branched lower alkyl group of from 1 to 4 carbon atoms; or alkenyl of 3 to 6 carbon atoms having the vinyl unsaturation in other than 1-position; and pharmaceutically acceptable acid addition salts thereof.

9 Claims, No Drawings

PHARMACEUTICALLY USEFUL OXYGEN CONTAINING HETEROCYCLIC DERIVATIVES

FIELD OF INVENTION

This invention relates to the use of bis-basic substituted oxygen containing heterocyclic derivatives.

DESCRIPTION OF THE PRIOR ART

Bis-basic ether and thioether derivatives of xanthene and xanthen-9-one are described in Belgian Patent No. 776,555. Bis-basic ester derivatives of dibenzofuran are described in Great Britain Patent No. 1,262,052 which is equivalent to pending U.S. application Ser. No. 833,717. Bis-basic ester derivatives of xanthene and xanthen-9-one are described in Netherlands Patent 72/09761 which is equivalent to pending U.S. application Ser. No. 162,716. Bis-basic ketone derivatives of dibenzofuran are described in South Africa Patent No. 71/5513 which is equivalent to pending U.S. application Ser. No. 72,171. Bis-basic ketone derivatives of xanthene and xanthen-9-one are described in Belgian Patent No. 776,535 which is equivalent to pending U.S. application Ser. No. 97,379. Each of these disclosures describe the compounds therein as being useful as antiviral agents and do not describe or suggest the use of the compounds in treating conditions of delayed hypersensitivity

SUMMARY OF INVENTION

Bis-basic derivatives of the following general formula are useful in the treatment of conditions of delayed hypersensitivity.

$$\underset{R^2}{\overset{R^1}{>}}N-A-Y-\underset{O}{\overset{X}{\bigodot\bigodot}}-Y-A-N\underset{R^2}{\overset{R^1}{<}}$$

Formula I

In the above genera Formula I, X represents a bond, $-CH_2-$ or carbonyl; Y represents a vinylene group, $$-\underset{\phantom{O}}{\overset{OH}{\underset{|}{C}H}}-,$$

carbonyl, oxygen, divalent sulfur or carbonyloxy with the proviso that when Y is $$-\underset{\phantom{O}}{\overset{OH}{\underset{|}{C}H}}-$$

or vinylene, X is other than carbonyl; A represents a straight or branched alkylene chain of from 1 to 6 carbon atoms with the proviso that when Y is vinylene, A contains from 1 to 5 carbon atoms, and with the proviso that when Y is carbonyloxy, A contains from 2 to 6 carbon atoms; each of $R^1$ and $R^2$ represents hydrogen, a straight or branched alkyl group of from 1 to 4 carbon atoms, or alkenyl of 3 to 6 carbon atoms having the vinyl unsaturation in other than the 1-position. Pharmaceutically acceptable acid addition salts of the compounds of Formula I are also included within the scope of this invention.

DETAILED DESCRIPTION OF INVENTION

As can be seen from general Formula I the compounds disclosed herein are dibenzothiophene derivatives when X represents a bond, or xanthene derivatives when X represents $-CH_2-$, or xanthen-9-one derivatives when X represents carbonyl.

In the above general Formula I one of the basic substituent groups as represented by $$-Y-A-N\underset{R^2}{\overset{R^1}{<}}$$

is attached at any carbon atom of one benzenoid ring of the tricyclic nucleus, and the other basic substituent is attached at any carbon atom of the other benzenoid ring.

Illustrative examples of straight or branched alkylene chains which A represents in general Formula I are methylene, ethylene, propylene, pentylene, hexylene, isobutylene, 2-methylethylene, 3-ethylbutylene and 2-methylpropylene.

Illustrative examples of straight or branched lower alkyl groups which $R^1$ and $R^2$ may represent are methyl, ethyl, propyl, isopropyl, n-butyl, isobutyl and tert-butyl.

Pharmaceutically acceptable acid addition salts of the base compounds of this invention are those of any suitable organic or inorganic acid. Illustrative suitable inorganic acids are hydrochloric, hydrobromic, sulfuric, and phosphoric acids. Illustrative suitable organic acids are lower aliphatic hydrocarbon monocarboxylic acids, such as, glycolic or lactic acid; lower aliphatic lower alkoxyhydrocarbon monocarboxylic acids, such as methoxyacetic or ethoxyacetic acids; lower aliphatic lower akanoylhydrocarbon monocarboxylic acids, such as, pyruvic acid; lower aliphatic hydrocarbon dicarboxylic acids, such as malonic, succinic, methylsuccinic, glutaric, α-methylglutaric, β-methylglutaric, itaconic, maleic, citraconic, homocitraconic, or fumaric acid; lower aliphatic hydroxy hydrocarbon dicarboxylic acids, such as, malic or tartaric acid; lower aliphatic lower alkoxy-hydrocarbon dicarboxylic acids, such as, α,β-dimethoxysuccinic or ethoxymaleic acid; lower aliphatic hydrocarbon tricarboxylic acids, such as, aconitic or tricarballylic acid; lower aliphatic hydroxy-hydrocarbon tricarboxylic acids, such as, citric acid. Additionally organic sulfonic acids, such as lower alkane sulfonic acids, for example, methanesulfonic or ethanesulfonic acid, or lower hydroxy-alkane sulfonic acids, for example, 2-hydroxyethane sulfonic acid are suitable. Particularly useful are pharmacologically acceptable acid addition salts with mineral acids, such as, hydrochloric acid. Mono- or di-acid salts may be formed, and the salts may be hydrated, for example monohydrate, or substantially anhydrous.

Illustrative examples of compounds of general Formula I are 2,8-bis(4-aminobutoxy)dibenzofuran, 3,7-bis(2-diethylaminoethoxy)dibenzofuran, 2,8-bis(2-diisopropylaminoethoxy)dibenzofuran, 2,8-bis(3-diallylaminopropoxy)dibenzofuran, 2,8-bis(5-di-n-propylaminopentoxy)dibenzofuran, 2,7-bis(3-dimethylamino-2-methylpropoxy)dibenzofuran, 1,7-bis(3-dimethylaminopropoxy)dibenzofuran, 3,6-bis(2-diethylaminoethoxy)xanthen-9-one, 3,6-bis(3-diallylaminopropoxy)xanthen-9-one, 3,6-bis(2-diethylaminoethylthio)xanthen-9-one, 2,7-bis(2-dimethylaminoethoxy)xanthene, 3,6-bis(2-aminoethoxy)xanthene, 2,7-bis(4-di-n-propylaminobutylthio)xanthene, 3,6-bis(5-diethylaminopentoxy)xanthene, 3,6-bis(6-dibutylaminohexyloxy)xanthene, 2,7-bis(3-dimethylaminopropylthio)xanthen-9-one, bis(3-diethylaminopropyl)-9-oxoxanthene-2,7-dicarboxylate, bis(3-diethylaminopropyl)xanthene-2,7-dicarboxylate, bis(3-di-n-butylaminopropyl)-9-oxoxanthene-2,7-dicarboxylate, bis(3-dimethylaminopropyl)xanthene-2,7-dicarboxylate, bis(5-dimethylamino-2-methylpentyl)xanthene-2,7-dicarboxylate bis(3-tert-butylaminopropyl)xanthene-1,7-dicarboxylate, bis(4-dithylaminobutyl)-9-oxoxanthene-4,5-dicarboxylate, bis(3-diethylaminopropyl)dibenzofuran-2,8-dicarboxylate, bis(3-dibutylaminopropyl)dibenzofuran-2,8-dicarboxylate, bis(3-diallylaminopropyl)dibenzofuran-2,8-dicarboxylate, bis(3-di-n-propylaminopropyl)-dibenzofuran-3,7-dicarboxylate, bis(2-diisopentylaminoethyl)dibenzofuran-4,6-dicarboxylate, 2,8-bis(2-diethylaminoacetyl)dibenzofuran, 2,8-bis(2-dimethylaminoacetyl)dibenzofuran, 4,6-bis(3-aminopropionyl)dibenzofuran, 3,7-bis(4-diethylaminobutyryl)dibenzofuran, 2,6-bis(5-diisopropylaminovaleryl)dibenzofuran, 2,7-bis(2-dimethylaminoacetyl)xanthene, 2,7-bis(2-diethylaminoacetyl)xathen-9-one, 2,6-bis(3-aminopropionyl)xanthene, 3,6-bis(4-diisopropylaminobutyryl)xanthene, 2,7-bis(5-diethylaminovaleryl)xanthene, 3,6-bis(3-dimethylaminopropionyl)xanthen-9-one, 2,7-bis(4-di-tert-butylaminobutyryl)xanthen9-one, α,α'-bis(3-diethylaminopropyl)xanthene-2,7-dimethanol, α,α'-bis(2-dimethylaminoethyl)xanthene-2,7-dimethanol, α,α'-bis(4-diisopropylaminobutyl)xanthene-3,6-dimethanol, α,α'-bis(dimethylaminomethyl)xanthene-2,7-dimethanol, α,α'-bis(2-dibutylaminoethyl)-dibenzofuran-2,8-dimethanol, α,α'-bis(3-dimethylaminopropyl)dibenzofuran-4,6-dimethanol, α,α'-bis(4-diethylaminobutyl)dibenzofuran-2,8-dimethanol, α,α'-bis(5-dimethylaminopentyl)dibenzofuran-2,8-dimethanol, 2,7-bis(4-dimethylamino-1-butenyl)xanthene, 2,7-bis(3-dimethylamino-1-propenyl)xanthene, 3,6-bis(5-diisopropylamino-1-pentenyl)xanthene, 2,8-bis(3-dibutylamino-1-propenyl)dibenzofuran, 4,6-bis(4-dimethylamino-1-butenyl)dibenzofuran, 2,8-bis(5-diethylamino-1-pentenyl)dibenzofuran, and 2,8-bis(6-dimethylamino-1-hexenyl)dibenzofuran.

Introduction of an antigen, or a foreign substance, into an organism results in a specific immunological response changing the reactivity of the organism towards the antigen and substances closely resembling the antigen. This response is usually a heightened reactivity to the antigen. This heightened reactivity is due in part to the production of antibodies which can result in an immediate hyerpsensitivity and in part to a cell-mediated immunity which can result in delayed hypersentitivity. Cell-mediated immunity is dependent upon the presence of cells sensitized to antigen, primarily thymus-modified lymphocytes, which specifically interact with the antigen. Macrophages are also involved in the processing of antigen and in the effector mechanisms leading to delayed hypersensitivity.

The type of substances which elicit delayed hypersensitivity are many and various. They may be organic chemicals, including drugs, simple chemical derivatives, or protein-containing antigens or micro-organisms, such as, bacteria, viruses, fungi or protozoa, or tissue antigens. Conditions of delayed hypersensitivity are associated with numerous pathological disorders, for example, contact hypersensitivity in the skin, rejection of tissue grafts or transplants, autoimmune diseases and certain infectious diseases. Such pathological disorders often involve, in addition to the cell-mediated delayed hypersensitivity responses, humoral antibody responses involving the production of antigen-specific antibodies. Generally, treatment of these disorders has been with immunosuppressive agents, such as, purine analogs, folic acid antagonists, alkylating agents and corticosteroids. Such agents have been found to be non-specific in their immunosuppressant effects, that is, they suppress both the humoral antibody ad delayed (cell-mediated) hypersensitivity responses. [Drug Therapy 1, no. 4, pp. 3–16 (1971)]. The compounds disclosed herein are unique in that they suppress only the delayed hypersensitivity response without concurrent suppression of the humoral immune responses.

The compounds disclosed herein suppress delayed hypersensitivity responses thereby rendering the compounds useful in patients in the treatment of conditions of delayed hypersensitivity resulting from infectious diseases, specifically tuberculosis, streptococcus, staphylococcus and pneumococcus diseases, typhoid fever, undulant fever, chancroid, whooping-cough and leprosy; toxoids and vaccines, particularly diphtheria toxoid and smallpox vaccination; contact hypersensitivity in the skin, specifically from nickel salts, primrose or poison ivy, poison oak and paraphenylene diamine; tissue grafts and transplants; and autoimmune diseases, specifically rheumatoid arthritis, systemic lupus erythematosus, glomerular nephritis, rheumatic fever, ulcerative colitis, diabetes mellitus, pernicious anemia, coeliac disease, primary atypical pneumonia, Hashimoto's thyroiditis, multiple sclerosis, peripherial neuritis, pemphigus, Addison's disease and Grave's disease.

The utility of the compounds disclosed herein in the treatment of conditions of delayed hypersensitivity is manifested by the ability of the compounds to suppress delayed hypersensitivity reactions in vitro in the macrophage migration inhibition (MMIT) test and in vivo in the experimental allergic encephalomyelytis (EAE) test which are well recognized tests for detecting agents or compounds effective in treating conditions of delayed hypersensitivity. *Immunology for Students of Medicine*, 3rd edition, 1970, F. A. Davis Company, pp, 498–500; Federation Proceedings 27, No. 1, pp. 3–15, (1968); Advances in Immunology 5, pp, 131–208 (1966).

As used herein, the term patient means warm blooded animals, particularly mammals and humans. The compounds disclosed herein may be administered orally, parenterally or topically either alone or in the form of pharmaceutical preparations. Pharmaceutical preparations containing conventional pharmaceutical carriers and as active ingredients compounds of this invention can be employed in unit dosage forms such as solids, for example, tablets, capsules and pills, or liquid solutions, suspensions, or emulsions for oral and parenteral administration. The quantity of compound administered can vary over a wide range to provide from about 0.1 mg/kg (milligrams per kilogram) to about 200mg/kg of body weight of the patient per day, and preferably from about 1 mg/kg to 100mg/kg of body weight of the patient per day, to achieve the desired effect. Unit doses can contain from about 5 mg to 1.0 g of a compound of this invention and may be administered, for example, from 1 to 4 times daily.

The compounds of general Formula I may be prepared by several methods. The compounds of general Formula I wherein Y is oxygen, that is, bis-basic ether derivatives of dibenzofuran, xanthene and xanthen-9-one may be prepared by the reaction of one equivalent of a diol derivative of the formula

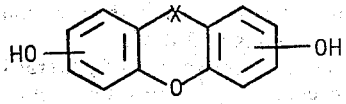

Formula II wherein X represents a bond, —CH$_2$— or carbonyl with 2 equivalents of an ω-haloalkylamine of the formula

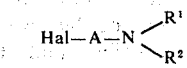  Formula III wherein Hal represents chlorine, bromine or iodine; A is a straight or branched alkylene chain of from 1 to 6 carbon atoms; and each of R$^1$ and R$^2$ is hydrogen, a straight or branched lower alkyl group of from 1 to 4 carbon atoms, or alkenyl of 3 to 6 carbon atoms having the vinyl unsaturation in other than the 1-position; in the presence of a base. Typical haloalkylamines are, for example, N,N-diethyl-2-chloroethylamine or N,N-diisopropyl-3-chloropropylamine.

Alternatively the bis-basic ether derivatives of general Formula I may be prepared by the reaction of a bis-ω-haloalkylether derivative of the formula

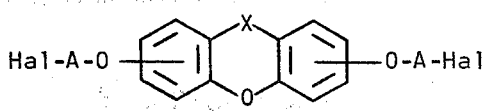

Formula IV wherein X, and A and Hal have the meanings defined hereinbefore, with an amine of the formula

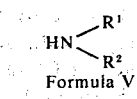

Formula V wherein R$^1$ and R$^2$ have the meanings defined hereinbefore. The bis-ω-haloalkylethers of Formula IV are obtained by the reaction of a diol derivative of dibenzofuran, xanthene aor xanthen-9-one with a haloalkylhalo derivative, that is, Hal-A-Hal wherein A is a straight or branched alkylene chain of from 1 to 6 carbon atoms and Hal is chlorine, bromine or iodine in the presence of a base.

Suitable bases for the above described reactions are sodium methoxide, sodium hydride, sodium amide, sodium hydroxide, and potassium hydroxide. Suitable solvents include aromatic hydrocarbons, such as benzene, toluene and xylene; halogenated aromatics, such as chlorobenzene; aprotic solvents, such as, N,N-dimethylformamide, N,N-dimethylacetamide, and dimethylsulfoxide; alcohols, such as, ethanol or isopropyl alcohol; ketones, such as acetone; ethers, such as, tetrahydrofuran or dioxane; water; or mixtures of these solvents.

When either sodium methoxide, sodium amide or sodium hydride, for example, is used as the base, the reaction is carried out in a anhydrous medium, such as anhydrous toluene or chlorobenzene. About 2.5 equivalents of the base is added to a suspension of the appropriate diol derivative, in the anhydrous solvent, and the mixture heated to form the diphenoxide In the case where sodium methoxide is used, the methanol formed may be removed advantageously by azeotropic distillation. About 2.5 equivalents of the halide, either a haloalkylamine or a haloalkylhalo derivative is added and the mixture heated to reflux for a period which may vary from about 4 to 24 hours. The products are isolated by customary procedures.

In the method where an alkali hydroxide, such as potassium hydroxide is used as the base, two different procedures may be used. In the one procedure a 25 to 50 per cent aqueous solution of the alkali hydroxide (about 2.5 equivalents) is added to a suspension of the diol derivative in a suitable aromatic solvent, for example, xylene. This mixture is then heated to boiling, stirring being optional, and the water removed by azeotropic distillation. The reaction mixture, now being essentially anhydrous, is treated with about 2.5 equivalents of either a haloalkylamine or a haloalkylhalo derivative. In the other procedure the reaction is carried out in a heterogenous medium of water and an aromatic hydrocarbon, such as, toluene or xylene. For example, one equivalent of the diol derivative is suspended in the aromatic hydrocarbon. To this suspension is added about 2.5 equivalents of a hydrohalide salt of a haloalkylamine derivative or a haloalkylhalo derivative in a minimum volume of water after which a 25 to 50% solution of the alkali hydroxide (about five equivalents when using a haloalkylamine derivative and about two equivalents when using a haloalkylhalo derivative) is added with efficient stirring. This mixture is heated to reflux for about 6 to 24 hours, and the product is isolated from the hydrocarbon layer.

The reaction between the bis-ω-haloalkylether derivative of Formula IV and an amine as represented by Formula V may be carried out under a variety of conditions. For example, the compound of Formula IV may be heated together with a large excess of the amine, the excess amine serving as both the reaction medium and the hydrohalide acceptor. Or, 1 equivalent of the bis(ω-haloalkyl)ether and 4 equivalents of the amine may be heated together in one of a number of different types of solvents, for example, in aromatic solvents, such as, benzene, toluene, xylene, or chlorobenzene; or lower molecular weight alcohols, such as, methanol, ethanol or isopropyl alcohol; or lower molecular weight ketones, such as, acetone or methyl ethyl ketone. The reaction between the halo compound and the amine is usually promoted by the addition of either sodium or potassium iodide, the iodide being used in either catalytic or stoichiometric amounts. In some cases, it may be advantageous to use only two equivalents of the amine for each equivalent of the bis-ω-haloalkylether, an excess of either powdered potassium carbonate or sodium carbonate being used as the hydrohalide acceptor.

The compounds of general Formula I wherein Y is divalent sulfur, that is, bis-basic thioether derivatives of dibenzofuran, xanthene and xanthen-9-one may be prepared by the same procedure described above for the preparation of the bis-basic ether derivatives of general Formula I upon substitution of the appropriate starting materials. By substituting an appropriate dibenzofurandiol, xanthenedithiol or a dimercaptoxanthen-9-one for the diol derivative of general Formula II and by substituting for derivative bis-ω-haloalkylether derivatives of Formula IV a derivative of the formula

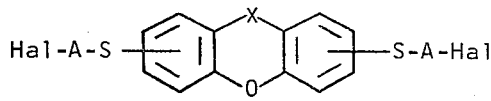

Formula VI wherein X is a bond, —CH$_2$— or carbonyl, A is a straight or branched alkylene chain of from 1 to 6 carbon atoms, and Hal is chlorine, bromine, or iodine, in the above described procedures for preparing bis-basic ether derivatives, the bis-basic thioether derivatives of dibenzofuran, xanthene and xanthen-9-one described herein may be prepared.

The compounds of general Formula I wherein Y is carbonyloxy, that is, bis-basic ester derivatives of dibenzofuran, xanthene and xanthen-9-one may be prepared by several methods. For example, a dicarboxylic acid or a reactive derivative thereof, such as, an acid halide or ester of the formula

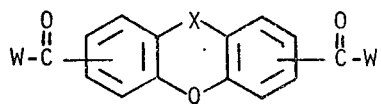

Formula VII wherein X is a bond, —CH$_2$—, or carbonyl; W is OH, halogen, such as, chlorine or bromine, or lower alkoxy, such as, methoxy or ethoxy, is reacted with an aminoalkanol of the formula

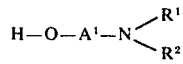

Formula VIII wherein A$^1$ is a straight or branched alkylene chain of from 2 to 6 carbon atoms and each of R$^1$ and R$^2$ is hydrogen, a straight or branched lower alkyl group of from 1 to 4 carbon atoms, or alkenyl of 3 to 6 carbon atoms having the vinyl unsaturation in other than the 1-position. The esterification can be achieved by allowing a derivative of Formula VII wherein W is hydroxy to react with the appropriate aminoalkanol in an inert solvent in the presence of a catalyst and employing general methods for removing water from the reaction site. Preferred solvents are chloroform, isopropyl alcohol, dioxane, and toluene. The reaction may be catalyzed by the use of mineral acids including hydrochloric, sulfuric or certain organic acids such as p-toluenesulfonic acid. Methods whereby water can be removed from the reaction include the use of water scavengers such as the carbodiimides or by the azeotropic removal of water. The reaction will proceed at temperatures ranging from 50°–250°C over a period of 6 to 72 hours depending upon the solvent and catalyst.

Preferably, the esterification can be achieved by allowing the acid halide, where W in the above Formula VII is halogen, to react with the appropriate aminoalkanol. The esters of this invention can be produced in a variety of inert solvents over a wide range of temperatures and reaction time. The solvents of choice include chloroform, dioxane, tetrahydrofuran, and the aromatic solvents such as benzene and toluene. In chloroform, the reaction is generally complete with one hour at a temperature of from 20°C to the reflux temperature of the solvent, although the reaction time can range from 15 minutes to 3 days.

The bis-basic ester derivatives of general Formula I may also be prepared by a transesterification reaction in which a derivative of Formula VII wherein W is lower alkoxy, for example, methoxy or ethoxy, is reacted with the appropriate aminoalkanol under suitable conditions. This type of reaction is catalyzed by alkaline or acid catalysts and is reversible. The basic esters may be obtained by causing the equilibrium to be shifted by removing the lower alkanol component or by employing a large excess of the aminoalkanol. Preferably, the reaction is carried out by removing the lower alkanol component with the use of an alkaline catalyst. The lower alkanol may be removed by direct distillation or distillation with a suitable solvent. Suitable alkaline catalysts are alkali metals, such as, sodium or potassium; alkali lower alkoxides, such as, sodium methoxide or sodium ethoxide; or alkali amides such as lithium or sodium amide. Suitable solvents are those forming an azeotropic distillation mixture with the lower alkanol, for example, benzene, or toluene, or a solvent which boils sufficiently higher than the alkanol to permit removal of the alkanol by distillation at a temperature below that of the boiling range of the solvent.

The compounds of general Formula I wherein Y is carbonyl, and X is a bond or —CH$_2$— may be prepared by an amination reaction of a bis-ω-haloalkanoyl derivative of the formula

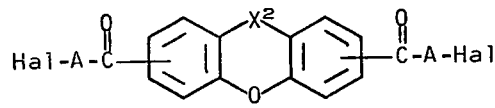

Formula IX wherein Hal is chlorine, bromine or iodine; A is a straight or branched alkylene chain of from 1 to 6 carbon atoms; and X$^2$ is a bond or —CH$_2$—; with an amine of the formula HNR$^1$R$^2$ wherein each of R$^1$ and R$^2$ have the meanings defined in general Formula I.

The amination reaction may be carried out under a variety of conditions. For example, a compound of Formula IX may be heated together with a large excess of the amine, the excess amine serving as the reaction medium and the hydrohalide acceptor. This method is particularly suitable for readily available amines, the excess of which can be easliy removed from the reaction mixture by, for example, distillation at reduced pressure or by washing the product with water. Or, one equivalent of a compound of Formula IX and four equivalents of the amine, may be heated together in one of a number of different types of solvents, for example, in aromatic solvents, such as, benzene, toluene, or xylene, ethers, such as, tetrahydrofuran, or dioxane; ketones, such as, acetone or butanone; aprotic solvents, such as, N,N-dimethylformamide, N,N-dimethylacetamide, or dimethyl sulfoxide; or mixtures of these solvents with water. The reaction between a compound of Formula IX wherein Hal is Cl and the amine, is frequently promoted by the addition of either sodium iodide or potassium iodide, the iodide being used in either catalytic or stoichiometric amounts. In some cases, it may be advantageous to use only two equivalents of the amine for each equivalent of the bis-ω-haloalkanoyl derivative, an excess of an inorganic base, such as, powdered sodium carbonate or potassium carbonate being used as the hydrohalide acceptor. The reaction will proceed normally in 12 hours to 2 weeks at temperatures of from −30° to 150°C.

Alternately, the amination reaction may be carried out on a derivative of a compound of Formula IX, such as, the bis-ketal derivative that may be prepared by allowing the bis-ω-haloalkanoyl derivative and an excess of ethyl orthoformate to react in the presence of an acid catalyst such as hydrochloric acid for several days in a polar solvent such as ethanol or tetrahydrofuran. The aminoketal derivative is hydrolyzed to the bis-basic ketone derivative of dibenzofuran or xanthene by warming with dilute acid.

The bis-(ω-haloalkanoyl)dibenzofuran derivatives, that is, compounds of Formula IX wherein $X^2$ is a bond, wherein the position of substitution is 2,6- or 2,8-can be prepared by a Friedel-Crafts acylation of dibenzofuran. Suitable acylating agents which may be used include chloroacetyl chloride, bromoacetyl bromide, 3-chloropropionyl chloride, 4-chlorobutyryl chloride, 5-chlorovaleryl chloride, 5-chloro-4-methylvaleryl chloride, and 5-chloro-3-methylvaleryl chloride.

The acylation reaction may be carried out in a variety of solvents and under catalysis of a variety of Lewis acids. The temperature and duration of the reaction may be varied to allow for optimum reaction conditions. A preferred procedure is to combine one equivalent of dibenzofuran with 2.5 equivalents of an acylating agent in methylene chloride followed by portionwise addition of aluminum chloride. The temperature of the reaction is maintained below zero degrees with continuous stirring. After the additions are complete the temperature may be elevated to 25°–40°C for 12 to 36 hours. The reaction mixture is worked up in the usual manner by decomposing the complex with ice water/HCl. The product obtained is recrystallized from methylene chloride, chloroform, or the like. The procedure may be varied such that there is a reverse addition of acylating agent and Lewis acid, or a reverse addition of aromatic hydrocarbon and Lewis acid. The more reactive halogen derivative, that is, the bis-(ω-iodoalkanoyl)dibenzofuran, may be prepared from the corresponding bischloro derivative using a halogen exchange reaction under the conditions generally employed in the Conant-Finkelstein reaction.

The bis-(ω-haloalkanoyl)xanthene derivatives, that is, compounds of Formula IX wherein $X^2$ is —CH$_2$— wherein the position of substitution is 2,7-may be prepared in the same manner as described for the preparation of the bis-(ω-haloalkanoyl)dibenzofuran derivatives, by substituting xanthene for dibenzofuran in the acylation reaction.

Suitable amines for use in the amination reaction include ammonia, or a compound which is a potential source of ammonia, for example, hexamethylenetotramine; primary amines, such as, ethylamine, propylamine and methylamine; and secondary amines, such as, diethylamine, dibutylamine diisopropylamine and dipentylamine.

The bis-basic ketone derivatives of Formula I wherein X is a bond, A is an alkylene chain of 3 to 6 carbon atoms, and $R^1$ and $R^2$ are other than hydrogen may also be prepared by the reaction of a dinitrile derivative of dibenzofuran with a Grignard reagent of the formula $R^5Mg(CH_2)_mNR^3R^4$  Formula X wherein $R^5$ is bromine or chlorine, $m$ is an integer of 3 to 6, and each of $R^3$ and $R^4$ is a straight or branched lower alkyl group of from 1 to 4 carbon atoms or alkenyl of 3 to 6 carbon atoms having the vinyl unsaturation in other than the 1-position. The reaction will proceed in from 1 to 24 hours at a temperature ranging from room temperature to about 80°C. The Grignard reagent, may be prepared by reacting magnesium and an aminoalkyl halide of the formula $R^5(CH_2)_mNR^3R^4$ wherein $R^5$, $m$, and —NR$^3$R$^4$ have the meaning defined hereinabove. A preferred solvent for this reaction is tetrahydrofuran. The dinitrile derivative of dibenzofuran may be prepared from known diamines by a Sandmeyer reaction on the tetrazonium salts or from known dibenzofuran dicarboxylic acids by dehydration of the corresponding amides by standard procedures.

The bis-ketone derivatives of Formula I wherein X is —CH$_2$—, A is an alkylene chain of from 3 to 6 carbon atoms and $R^1$ and $R^2$ are other than hydrogen may also be prepared by the reaction of a Grignard reagent of the above Formula X with a bis-ester or bis-amide derivative of xanthene of formula

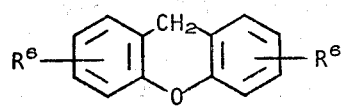

Formula XI wherein $R^6$ is

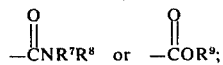

$R^7$ and $R^8$ represent hydrogen or lower alkyl, or NR$^7$R$^8$ taken together form a saturated monocyclic heterocyclic group such as piperidino or pyrrolidino; $R^9$ represents a straight or branched lower alkyl group or an aryl group such as phenyl or benzyl. The addition of the Grignard reagent, is carried out at low temperatures ranging from −70°C to 0°C, and the reaction mixture is then warmed at 0°C to 80°C for 1 to 24 hours. The xanthene bis-amide derivatives of Formula XI may be prepared by generally known methods from the corresponding bis-acids. These may be obtained among other procedures by reduction of the corresponding xanthen-9-one bis-acids by known methods such as the Wolff-Kishner reduction or by reduction with sodium and alcohol. The xanthen-9-one bis-acids may be prepared by oxidation of the corresponding dimethylxanthenes [T. Sengoku, J. Pharm. Soc. Japan 53, 962 (1933); M. Schopff, Ber. 25, 3647 (1892)], by oxidation of higher fused ring analogs [O. Kruber, Ber. 74B, 1688 (1941)] or by the generally known oxidation of a corresponding diacetyl derivative with hypochlorite and the like.

The bis-basic ketone compounds of general Formula I wherein A is —CH₂CH₂— both of R¹ and R² are not hydrogen and X is a bond or —CH₂— may also be prepared by a Mannich reaction of a bis-acetyl derivative of the formula

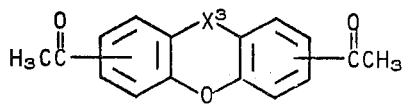

Formula XII wherein X³ is a bond, or —CH₂—, with an amine of the formula HNR¹R² wherein R¹ and R² have the meanings defined in general Formula I except that both of R¹ and R² are not hydrogen, in the presence of formaldehyde. By combining one equivalent of a compound of Formula XII and two or more equivalents the amine with three or more equivalents of formaldehyde the reaction will proceed in from a few minutes to 24 hours in solvents such as water, acetic acid, ethanol, butanol, dioxane, and tetrahydrofuran and at temperatures equivalent to the reflux temperature of the solvent. In this reaction either of two sources of formaldehyde may be employed. When formalin is used the reaction may be conducted with a suspension of a compound of Formula XII or a co-solvent such as methanol may be added to allow the reaction to proceed in a homogeneous medium. When the source of formaldehyde is paraformaldehyde the reaction is carried out in an organic solvent such as those mentioned above. It is sometimes desirable to add a slight excess of hydrochloric acid to promote depolymerization or paraformaldehyde either during the reaction or at the end of the reaction.

The amine employed in this reaction may be added to the reaction medium as the hydrochloride salt or as the base form with subsequent in situ formation of the hydrochloride salt by the addition of hydrochloric acid. Typical amines which may be utilized in the above reaction include dimethylamine, dibutylamine, n-propylamine, diisopropylamine and methylamine.

The bis-acetyl derivatives of Formula XII may be prepared by a Friedel-Crafts acylation reaction on dibenzofuran or xanthene. The bis-acetyl dibenzofuran derivative may also be prepared by a Griganrd reaction of dicyanodibenzofuran with methylmagnesium halide. The dicyanodibenzofuran derivative may be obtained by methods described hereinabove. Also, the bis-acetyl xanthene derivative may be prepared by a Grignard reaction of a xanthene bis-amide or bis-ester derivative of Formula XI with methylmagnesium halide. The xanthene bis-amide and bis-ester derivatives may be prepared by means described hereinabove.

The bis-basic ketone derivatives of general Formula I wherein X is carbonyl may be prepared by oxidation of the corresponding xanthene bis-basic ketone compounds. This oxidation reaction may be carried out using dichromate anion such as sodium dichromate or potassium dichromate as the oxidizing agent. The reaction will proceed in from 15 minutes to 6 hours at a temperature of from 80° to 120°C. The amount of oxidizing agent is limited to the stoichiometric quantity required for oxidation of the 9-methylene group of the xanthene derivative. Suitable solvents for this conversion are, for example, water, acetic acid and tert-butyl alcohol, or combinations of these solvents. For example, by combining three moles of a compound of general Formula I, wherein X is —CH₂— and Y is carbonyl, dissolved in acetic acid with four moles of sodium dichromate and refluxing the mixture for 1 to 3 hours, the corresponding xanthen-9-one derivative is obtained.

The compound of general Formula I wherein Y is

and X is a bond or —CH₂— are obtained by the reduction of the corresponding ketone derivatives, that is, compounds of Fromula I wherein Y is carbonyl and X is a bond or —CH₂—, the preparation of which is described hereinabove, using sodium borohydride as the reducing agent. Suitable solvents for this reaction are ethers, such as, tetrahydrofuran or dioxane, lower alcohols, such as, methanol or isopropyl alcohol, or water. The reaction time may vary from about 30 minutes to 25 hours, and the reaction temperature may vary from about —20°C to 100°C. When water or methanol are used as solvents, a base such as sodium hydroxide is used in order to minimize the rate at which the sodium borohydride decomposes.

The compounds of general Formula I wherein Y is a vinylene group and X is a bond or —CH₂— are prepared by dehydration of a compound of Formula I wherein Y is

A contains 2 or more carbon atoms, and X is a bond or —CH₂—, the preparation of which is described above. Dehydration is accomplished by dissolving the bis-alkanol derivative in a high boiling solvent such as ethylene glycol monoethylether, adding a dehydrating agent, such as, concentrated HCl or concentrated H₂SO₄, then heating the reaction mixture to about 100°C on a steam bath for from 1 to 30 minutes. The vinylene derivatives may be isolated and purified by standard procedures. For example, the reaction mixture can be made alkaline and the product extracted with ether; or, any unreacted starting material may be separated from the final product by passage through a chromatographic column.

The following specific examples are illustrative of compounds of general Formula I.

EXAMPLE 1

2,8-Bis(2-diethylaminoethoxy)dibenzofuran dihydrochloride

To 200 ml of water containing 13.0 g (0.33 mole) of sodium hydroxide and 12.0 g (0.06 mole) of 2,8-dihydroxydibenzofuran are added 250 ml of toluene and 26.0 g (0.15 mole) of 2-diethylaminoethyl chloride hydrochloride, and the heterogeneous reaction mixture is heated to reflux with stirring for 24 hours. When cool, the organic layer is washed with water, dried over magnesium sulfate then concentrated in vacuo. The remaining oily residue is dissolved in ether and treated with ethereal HCl to give 2,8-bis(2-diethylaminoethoxy)dibenzofuran dihydrochloride which is recrystallized twice from methanol-ethyl acetate. M.P. 236.5°–283.5°C.

EXAMPLE 2

2,8-Bis(3-diethylaminopropoxy)dibenzofuran

Following the procedure of Example 1, only substituting for 2-diethylaminoethyl chloride hydrochloride, 27.9 g (0.15 mole) of 3-diethylaminopropyl chloride hydrochloride, 2,8-bis(3-diethylaminopropoxy)dibenzofuran is obtained as an oil after subsequent chromatography of the product on alumina using chloroform as the eluant. $\lambda_{max}^{EtOH}$ 305, $E_{1cm}^{1\%}$ 455.

EXAMPLE 3

2,8-Bis(3-dimethylaminopropoxy)dibenzofuran dihydrochloride

To 400 ml of chlorobenzene are added 14.2 g (0.05 mole) of dibenzofuran-2,8-diol diacetate, 10.8 g (0.2 mole) of sodium methoxide and 15.8 g (0.1 mole) of 3-dimethylaminopropyl chloride hydrochloride. The mixture is heated to reflux with stirring for 24 hours, then cooled and filtered. The filtrate is washed with several portions of water and dried over magnesium sulfate. The chlorobenzene solution is evaporated in vacuo leaving an oily residue which is dissolved in ether and treated with ethereal HCl to give 2,8-bis(3-dimethylaminopropoxy)dibenzofuran dihydrochloride which is recrystallized from methanol-ethyl acetate. M.P. 257°–258°C.

EXAMPLE 4

2,8-Bis(2-dimethylamino-1-methylethoxy)dibenzofuran bis-dihydrogen citrate

Following the procedure of Example 1 only substituting for 2-diethylaminoethyl chloride hydrochloride 23.7 g (0.15 mole) of 2-dimethylaminoisopropyl chloride hydrochloride the free base of 2,8-(2-dimethylamino-1-methylethoxy)dibenzofuran is obtained and subsequently treated with a methanol solution of citric acid to give the bisdihydrogen citrate salt which is recrystallized twice from methanol-acetone. M.P. 120°–122°C.

EXAMPLE 5

2,8-Bis(3-dimethylamino-2-methylpropoxy)dibenzofuran dihydrochloride

Following the procedure of Example 3 only substituting for 3-dimethylaminopropyl chloride hydrochloride, 17.2 g (0.1 mole) of 3-dimethylamino-2-methylpropyl chloride hydrochloride, 2,8-bis(3-dimethylamino-2-methylpropoxy)dibenzofuran dihydrochloride is obtained and recrystallized 3 times from methanol-acetone. M.P. 126°–128°C.

EXAMPLE 6

2,8-Bis(2-diisopropylaminoethoxy)dibenzofuran

Following the procedure of Example 3 only substituting for 3-dimethylaminopropyl chloride hydrochloride, 20.0 g (0.1 mole) of 2-diisopropylaminoethyl chloride hydrochloride, 2,8-bis(2-diisopropylaminoethoxy)dibenzofuran is obtained after chromatography on alumina using chloroform as the eluant. M.P. 47°–49°C.

EXAMPLE 7

3,7-Bis(2-diethylaminoethoxy)dibenzofuran dihydrochloride

Following the procedure of Example 1 only substituting for 2,8-dihydroxydibenzofuran, 3,7-dihydroxydibenzofuran, 3,7-bis(2-diethylaminoethoxy)dibenzofuran dihydrochloride is obtained.

EXAMPLE 8

2,8-Bis(2-dihexylaminoethoxy)dibenzofuran dihydrochloride

Following the procedure of Example 1 only substituting for 2-diethylaminoethyl chloride hydrochloride, 42.6 g (0.15 mole) of 2-hexylaminoethyl chloride hydrochloride, 2,8-bis(2-dihexylaminoethoxy)dibenzofuran dihydrochloride is obtained.

EXAMPLE 9

2,8-Bis(2-ethylaminoethoxy)dibenzofuran dihydrochloride

A. With stirring, 80 ml of 10% aqueous sodium hydroxide is added dropwise, over a period of thirty minutes, to a mixture of 0.1 mole of 2,8-dihydroxydibenzofuran and 0.3 mole of 1-bromo-2-chloroethane in 400 ml of water. With continued stirring, the mixture is then heated to reflux for eighteen hours. When cool, the supernatant water layer is decanted and the residue dissolved in boiling ethanol. The solid which separates on cooling is filtered and recrystallized from ethanol-chlorofrom to yield 2,8-bis(2-chloroethoxy)dibenzofuran.

B. A mixture of 0.05 mole of 2,8-bis(2-chloroethoxy)dibenzofuran, 1.0 mole of ethylamine, 2.0 g potassium iodide and 100 ml of tetrahydrofuran is heated with stirring at 100°C for 24 hours in a Parr pressure reactor. The solvent and excess amine are removed in vacuo. The residue is treated with dilute sodium hydroxide and extracted with ether. The ether layer is washed twice with water, dried over anhydrous magnesium sulfate and acidified with ethereal HCl to give 2,8-bis(2-ethylaminoethoxy)dibenzofuran dihydrochloride which is recrystallized from methanol-ethyl acetate.

EXAMPLE 10

2,8-Bis(2-aminoethoxy)dibenzofuran dihydrochloride

Following the procedure of Example 9 (B), only substituting for ethylamine the appropriate molar equivalent amount of hexamine, 2,8-bis(2-aminoethoxy)dibenzofuran dihydrochloride is obtained after subsequent decomposition of the intermediate quaternary ammonium complex with dilute acid.

EXAMPLE 11

2,8-Bis(6-diethylaminohexyloxy)dibenzofuran dihydrochloride

Following the procedure of Example 9 (A), only substituting for 2-bromo-1-chloroethane, the appropriate molar equivalent amount of 6-bromo-1-chlorohexane, the intermediate, 2,8-bis(6-chlorohexyloxy)dibenzofuran, is prepared. Upon reacting this intermediate with an excess of diethylamine by the procedure of Example 9 (B), 2,8-bis(6-diethylaminohexyloxy)dibenzofuran dihydrochloride is obtained.

EXAMPLE 12

Following the procedure of Example 1 only substituting for 2,8-dihydroxydibenzofuran, 1,7- and 2,7-dihydroxydibenzofuran, the following compounds are obtained: 1,7-bis(2-diethylaminoethoxy)dibenzofuran 2,7-bis(2-diethylaminoethoxy)dibenzofuran.

EXAMPLE 13

3,6-Bis(2-diethylaminoethoxy)xanthen-9-one

A mixture of 23.0 g (0.1 mole) of 3,6-dihydroxyxanthen-9-one, 16.0 g (0.296 mole) of sodium methoxide, 350 ml of chlorobenzene and 60 ml of methanol is stirred and heated to 130°C. during which time methanol is distilled off and collected. After cooling the reaction mixture to less than about 100°C, 33.0 g (0.245 mole) of β-diethylaminoethyl chloride is added and the mixture refluxed for 5½ hours then cooled to 100°C after which 300 ml of water and 10 ml of 40% NaOH are added. For 20 minutes the mixture is stirred, then the chlorobenzene layer is separated, dried over anhydrous magnesium sulfate, filtered, treated with ethereal HCl, and the resulting precipitate recrystallized from methanol-ethyl acetate to give the dihydrochloride salt of the desired product. The dihydrochloride salt is treated with dilute NaOH, extracted into chloroform, dried over anhydrous magnesium sulfate, filtered and concentrated to give a solid which is recrystallized from hexane to give 3,6-bis(2-diethylaminoethoxy)xanthen-9-one. M.P. 70.5°–72°C.

EXAMPLE 14

3,6-Bis(2-dimethylaminoethoxy)xanthen-9-one

To 54.5 g (0.239 mole) of 3,6-dihydroxyxanthen-a-one is added 240 ml of methanol and 29.0 g (0.717 mole) of sodium methoxide with stirring after which 700 ml of chlorobenzene is added. Methanol is distilled off until the reaction temperature reached 130°C. After cooling the reaction mixture to less than about 100°C, 64.0 g (0.590 mole) of 2-dimethylaminoethyl chloride is added and the reaction mixture refluxed for 4½ hours followed by the addition of 600 ml of water and 20 ml of 50% NaOH with stirring continued for one-half hour. The mixture is cooled and chloroform is added to completely dissolve the product. The chlorobenzene-chloroform layer is separated and the aqueous layer is extracted into chloroform. The combined organic layers are washed with water, dried over anhydrous magnesium sulfate and evaporated to give a dark brown oil which solidifies upon cooling. The solid is dissolved in boiling ethanol, precipitated with water, cooled and filtered. The resulting solid is dried in vacuo and recrystallized from hexane to give 3,6-bis(2-dimethylaminoethoxy)xanthen-9-one. M.P. 87.5°–89°C.

EXAMPLE 15

3,6-Bis(2-diisopropylaminoethoxy)xanthen-9-one

Following the procedure of Example 14 only substituting for 2-dimethylaminoethyl chloride the appropriate molar equivalent amount of 2-(diisopropylamino)ethyl chloride, 3,6-bis(2-diisopropylaminoethoxy)xanthen-9-one is obtained after recrystallization from hexane. M.P. 117.5°–118°C.

EXAMPLE 16

3,6-Bis(3-dimethylaminopropoxy)xanthen-9-one

Following the procedure of Example 14, only substituting for 2-dimethylaminoethyl chloride the appropriate molar equivalent amount of 3-dimethylaminopropyl chloride, 3,6-bis(3-dimethylaminopropoxy)xanthen-9-one is obtained after recrystallization from hexane. M.P. 69°–70°C.

EXAMPLE 17

3,6-Bis(2-diethylaminoethylthio)xanthen-9-one dihydrochloride

A mixture of 34.0 g (0.0844 mole) of S,S'-(9-oxoxanthene-3,6-diyl)bis(dimethylthiocarbamate), 200 ml of methanol, 100 ml of 50% NaOH and 100 ml of water is refluxed under a nitrogen atmosphere until solution is complete, and 700 ml of chlorobenzene is added during which time methanol and water are removed by distillation. Upon cooling 37.5 g (0.278 mole) of diethylaminoethyl chloride is added, and the mixture is refluxed under a nitrogen atmosphere for 3 hours, stirred at room temperature for 49 hours then refluxed for an additional 5 hours. After cooling, 300 ml of 10% NaOH is added and the mixture stirred for one-half hour after which ether and chloroform are added. The organic layer which separates is washed with water, dried over magnesium sulfate and evaporated to give a brown oil. The oily material is dissolved in 100 ml ether, treated with ethereal HCl, and the resulting precipitate is filtered and recrystallized from ethanol to give 3,6-bis(2-diethylaminoethylthio)xanthen-9-one dihydrochloride. M.P. 227°–229°C.

EXAMPLE 18

2,7-Bis(2-dimethylaminoethoxy)xanthene

To 20 g (0.0935 mole) of 2,7-dihydroxyxanthene in 350 ml of chlorobenzene are added 16.5 g (0.3 mole) of sodium methoxide and 60 ml of methanol. The reaction mixture is stirred and heated during which time the methanol is removed by distillation. The mixture is cooled and 29 g (0.26 mole) of 2-dimethylaminoethyl chloride is added. After refluxing with stirring for 4 hours the mixture is cooled and 100 ml of water plus 10 ml of 50% NaOH solution are added. The mixture is stirred for 15 minutes and 100 ml of chloroform is added. The organic layer which separates is washed with 5% NaOH solution, then with wtaer, dried over anhydrous magnesium sulfate, filtered and concentrated to a solid residue which is recrystallized from hexane to give 2,7-bis(dimethylaminoethoxy)xanthene. M.P. 85°–86.5°C.

EXAMPLE 19

Bis(3-diethylaminopropyl)dibenzofuran-2,8-dicarboxylate dihydrochloride

To 2 liters of chloroform is added 14.5 g (0.05 mole) of dibenzofuran-2,8-dicarbonyl chloride and 13 g (0.1 mole) of 3-diethylaminopropanol, and the solution is heated at reflux for 12 hours. The reaction mixture is concentrated to about 500 ml, and the product is crystallized from chloroform-petroleum ether (75°–90°). A second crystallization from isopropyl alcohol gave bis(3-diethylaminopropyl)dibenzofuran-2,8-dicarboxylate dihydrochloride. M.P. 258°–259.5°C.

EXAMPLE 20

Bis(3-dibutylaminopropyl)dibenzofuran-2,8-dicarboxylate dihydrochloride hemihydrate A solution of 20 g (0.068 mole) of dibenzofuran-2,8-dicarbonyl chloride and 26.6 g (0.14 mole) of 3-dibutylaminopropanol in 750 ml of chloroform is heated at reflux for 6 hours. The solution is allowed to cool, diluted with ether and the product which separates on standing is collected by filtration and recrystalized twice from ethanol to give bis(3-dibutylaminopropyl)dibenzofuran-2,8-dicarboxylate dihydrochloride hemihydrate. M.P. 200°–202°C.

EXAMPLE 21

Bis(3-dimethylaminopropyl)dibenzofuran-2,8-dicarboxylate dihydrochloride hemihydrate A solution of 8.8 g (0.03 mole) of dibenzofuran-2,8-dicarbonyl chloride and 6.2 g (0.06 mole) of 3-dimethylaminopropanol in 400 ml of chloroform is refluxed for 16 hours. On cooling, the product crystallizes and after two recrystallizations from methanol-butanone, bis(3-dimethylaminopropyl)dibenzofuran-2,8-dicarboxylate dihydrochloride hemihydrate is obtained. M.P. 222.5°–224°C.

EXAMPLE 22

Bis(3-dipropylaminopropyl)dibenzofuran-2,8-dicarboxylate dihydrochloride hemihydrate In the procedure of Example 21, 3-dimethylaminopropanol is replaced by 9.6 g (0.06 mole) of 3-dipropylaminopropanol, and petroleum ether is added to the reaction mixture to yield bis(3-dipropylaminopropyl)dibenzofuran-2,8-dicarboxylate dihydrochloride hemihydrate. M.P. 222°–224°C.

EXAMPLE 23

Bis(3-diisopentylaminopropyl)dibenzofuran-2,8-dicarboxylate

When 3-diisopentylaminopropanol, 18.9 g (0.06 mole) is used in place of 3-dimethylaminopropanol and the procedure of Example 21 is followed, the diisopentylaminopropyl ester as the dihydrochloride salt is obtained. M.P. 171°–173°C. The salt is converted to the free base which is an opaque viscous oil, $\lambda_{max}^{0.1\ N\ HCl}$ 244, $E_{1cm}^{1\%}$ 1080.

EXAMPLE 24

Bis(3-diethylaminopropyl)dibenzofuran-3,7-dicarboxylate

Bis(3-diethylaminopropyl)dibenzofuran-3,7-dicarboxylate is prepared by the reaction of dibenzofuran-3,7-dicarbonyl chloride and 3-diethylaminopropanol, according to the procedure of Example 19.

EXAMPLE 25

Bis(3-diethylaminopropyl)dibenzofuran-4,6-dicarboxylate

Bis(3-diethylaminopropyl)dibenzofuran-4,6-dicarboxylate is prepared by the reaction of dibenzofuran-4,6-dicarbonyl chloride with 3-diethylaminopropanol, according to the procedure of Example 19.

EXAMPLE 26

Bis(3-diethylaminopropyl)-9-oxoxanthene-2,7-dicarboxylate dihydrochloride

To 14.2 g (0.05 mole) of xanthone-2,7-dicarboxylic acid is added 150 ml of (2.1 moles) of thionyl chloride and 100 ml of dry tetrahydrofuran. The resulting solution is refluxed for 3 hours, and then the solvent and excess thionyl chloride are removed at reduced pressure on a steam bath. The residue is dissolved in 500 ml of dry methylene chloride, treated with activated charcoal and filtered. To the filtrate, containing xanthone-2,7-dicarboxylic acid chloride, is added 17 g (0.13 mole) of 3-diethylaminopropanol. The resulting mixture is refluxed 1.5 hours and let stand for three days. The solvent is removed and the residue dissolved in dilute hydrochloric acid and washed with methylene chloride. The aqueous layer is made basic with 15% sodium carbonate solution and extracted with methylene chloride. This solution is washed with dilute sodium carbonate solution and water and then dried over anhydrous magnesium sulfate. Upon filtering, the solvent is removed under reduced pressure and the residue dissolved in isopropyl alcohol and converted to the dihydrochloride with ethanolic-HCl. The product is precipitated with diethylether, filtered and purified from isopropanol-methanol to give 8.7 g (29.8%) of bis-(3-diethylaminopropyl)-9-oxoxanthene-2,7-dicarboxylate dihydrochloride. M.P. 269.5°–270.5°C.

EXAMPLE 27

Bis(3-di-n-butylaminopropyl)-9-oxoxanthene-2,7-dicarboxylate dihydrochloride

Following the procedure of Example 26, 28.4 g (0.1 mole) of xanthone-2,7-dicarboxylic acid is converted to the corresponding diacid chloride and reacted with 38 g (0.21 mole) 3-di-n-butylaminopropanol to give 9.0 g (12.9%) of the dihydrochloride of bis(3-di-n-butylaminopropyl)-9-oxoxanthene-2,7-dicarboxylate. M.P. 222.5°–223.5°C from isopropanol.

EXAMPLE 28

Bis-(3-di-n-butylaminopropyl)xanthene-2,7-dicarboxylate dihydrochloride

To 17.4 g (0.06 mole) of xanthene-2,7-dicarboxylic acid is added 100 ml (1.4 moles) of thionyl chloride and 4 drops of pyridine. The resulting solution is refluxed for four hours, and solvent and excess thionyl chloride are removed. The intermediate diacid chloride in benzenemethylene chloride is reacted with 24 g (0.13 mole) of 3-di-n-butylaminopropanol by refluxing for 3 hours. Most of the solvent is removed and the residue allowed to stand for two days. The residue is diluted with methylene chloride and 10% hydrochloric acid. The organic layer and two methylene chloride washings of the aqueous layer are combined and dried over anhydrous magnesium sulfate. The solution is filtered and concentrated at reduced pressure to a solid residue. This is purified from isopropyl alcohol to give 12.9 g (19.6%) of bis(3-di-n-butylaminopropyl)xanthene-2,7-dicarboxylate dihydrochloride. M.P. 187.5°–190°C.

EXAMPLE 29

Following the procedure of Example 28 only substituting for 3-di-n-butylaminopropanol an appropriate molar equivalent amount of 5-dimethylamino-2,2-dimethylpentanol or 4-diisopropylaminobutanol, the following respective products are obtained:

bis(5-dimethylamino-2,2-dimethylpentyl)xanthene-2,7-dicarboxylate, bis(4-diisopropylaminobutyl)xanthene-2,7-dicarboxylate.

EXAMPLE 30

2,8-Bis(diethylaminoacetyl)dibenzofuran dihydrochloride hemihydrate

To a mixture of 25.0 g (0.078 mole) of 2,8-bis(chloroacetyl)dibenzofuran and 100 ml of tetrahydrofuran, cooled in an ice/water bath, is added 100 ml of diethylamine over a 20 minute period. The mixture is refluxed gently for 24 hours then filtered while hot. The solvent is removed in vacuo, and the remaining residue is slurried with ether and filtered. The filtrate is treated with ethereal HCl. The resulting precipitate is collected and recrystallized from methanol-ether then from ethanol-ether to give 2,8-bis(diethylaminoacetyl)dibenzofuran dihydrochloride hemihydrate. M.P. 225°–227°C. (dec).

EXAMPLE 31

2,8-Bis(dimethylaminoacetyl)dibenzofuran dihydrochloride dihydrate

A mixture of 24.5 g (0.076 mole) of 2,8-bis(chloroacetyl)dibenzofuran, 350 ml of tetrahydrofuran and 30.0 g (0.668 mole) of dimethylamine (gas) is heated at 60°C for 24 hours in a Parr pressure bomb. Upon cooling to room temperature the mixture is filtered and the filtrate dried in vacuo. The remaining residue is slurried with ether, filtered, and the filtrate is treated with ethereal HCl. The resulting precipitate is collected and recrystallized from ethanol-butanone to give 2,8-bis(dimethylaminoacetyl)dibenzofuran dihydrochloride dihydrate. M.P. >330°C.

EXAMPLE 32

Following the procedure of Example 30 only substituting for 2,8-bis(chloroacetyl)dibenzofuran, appropriate molar equivalent amounts of 2,6-bis(4-chlorobutyryl)dibenzofuran, which is prepared by an acylation reaction of dibenzofuran and 4-chlorobutyryl chloride, or substituting 2,8-bis(3-chloropropionyl)dibenzofuran, which is prepared by an acylation reaction of dibenzofuran and 3-chloropropionyl chloride, the following respective products are obtained:

2,6-bis(4-diethylaminobutyryl)dibenzofuran dihydrochloride, 2,8-bis(3-diethylaminopropionyl)dibenzofuran dihydrochloride.

EXAMPLE 33

4,6-Dicyanodibenzofuran

To a mixture of one equivalent of 4,6-dibenzofurandicarboxylic acid [H. Gilman and R. Young, J. Am. Chem. Soc. 57, 1121 (1935)] and 2.2 equivalents of p-toluenesulfonamide is added 4.5 equivalents of phosphorous pentachloride. When the initial reaction subsides the reaction mixture is heated to 200°C. and the solid residue remaining is cooled and treated with pyridine and water. The suspension is filtered, washed with water and suspended in dilute sodium hydroxide solution followed by filtration and washing with water to give 4,6-dicyanodibenzofuran which can be recrystallized from a dimethylformamide-water combination. In like manner 3,7-dicyanodibenzofuran is prepared from 3,7-dibenzofurandicarboxylic acid [H. Sugii and H. Shindo, J. Pharm. Soc. Japan 54, 829 (1934)].

EXAMPLE 34

4,6-Bis(4-dibutylaminobutyryl)dibenzofuran dihydrochloride

To a solution of 2.5 equivalents of 3-dibutylaminopropyl magnesium chloride, prepared from magnesium and 3-dibutylaminopropylchloride in tetrahydrofuran, is added dropwise a solution of 1 equivalent of 4,6-dicyanodibenzofuran dissolved in tetrahydrofuran. After the addition is complete the reaction mixture is gently refluxed for 2 hours then stirred at room temperature for 6 hours. The Grignard complex is decomposed by treating the reaction mixture with saturated ammonium chloride, and the organic material is extracted with chloroform. The chloroform layer is treated with dilute hydrochloric acid with warming, then the aqueous solution is filtered, cooled, made alkaline and extracted with several portions of ether. The ether extracts are combined, dried over magnesium sulfate and treated with ethereal HCl to yield 4,6-bis(4-dibutylaminobutyryl)dibenzofuran dihydrochloride which is purified by crystallization from methanol-ethyl acetate.

EXAMPLE 35

2,7-Bis(2-dimethylaminoacetyl)xanthene dihydrochloride

To an ice cold mixture of 33.5 g (0.01 mole) 2,7-bis(2-chloroacetyl)xanthene, 2 g of potassium iodide in 150 ml of tetrahydrofuran in a Parr bomb is added an ice cold solution of dimethylamine and 150 ml of tetrahydrofuran. The resulting mixture is warmed to room temperature and stirred for 7 days, filtered and the filtrate evaporated to dryness. The residue is dissolved in 10% HCl, filtered and the filtrate is made alkaline. The resulting solid is extracted with methylene chloride, acidified with ethereal HCl to Congo Red, filtered, recrystallized twice from methanol-diethyl ether, and dried to give 2,7-bis(2-dimethylaminoacetyl)xanthene dihydrochloride. M.P. >350°C.

EXAMPLE 36

2,7-Bis(2-diethylaminoacetyl)xanthen-9-one

To a mixture of 2,7-bis(2-bromoacetyl)xanthen-9-one in tetrahydrofuran is added diethylamine, each cooled to −20°C. The reaction mixture is maintained at −20°C for 24 hours then allowed to warm slowly to room temperature and maintained at room temperature for 5 days. The mixture is filtered, and the filtrate evaporated to dryness. The resulting residue is dissolved in dilute HCl, filtered and the filtrate is made alkaline, keeping the temperature of the mixture around 0°C. The mixture is extracted with methylene chloride, and the extract acidified to Congo Red. The resulting solid is filtered off and recrystallized from methanol-diethylether to give 2,7-bis(2-diethylaminoacetyl)xanthen-9-one.

The preparation of additional examples of bis-basic ketone derivatives of xanthene and xanthen-9-one and appropriate starting materials are set forth in Belgian Pat. No. 776,535, which is equivalent to pending U.S.

application Ser. No. 97,379, and of which the appropriate examples are incorporated herein by reference thereto.

EXAMPLE 37

α,α'-Bis(3-diethylaminopropyl)xanthene-2,7-dimethanol

To a cooled, stirred solution of 24.6 g (0.053 mole) of 2,7-bis(4-diethylaminobutyryl)xanthene, which is prepared by an amination reaction of 2,7-bis(4-chlorobutyryl)xanthene with diethylamine, dissolved in 200 ml of tetrahydrofuran is added a solution of 4.2 g (0.11 moles) of sodium borohydride contained in a solution of methanol and 5 ml of 10% sodium hydroxide solution. The resulting mixture is allowed to warm gradually to room temperature and stirring continued overnight. The reaction mixture is diluted with water and the solid which forms is filtered, washed with water and air dried. The solid product is dissolved in a 10% hydrochloric acid solution, filtered and the filtrate made alkaline with a 10% sodium hydroxide solution. The alkaline filtrate is extracted with methylene chloride. The organic extract is then washed with water, followed by a wash of saturated sodium chloride solution, dried over anhydrous magnesium sulfate, filtered and evaporated to dryness in vacuo. The residue is recrystallized from benzene to give α,α'-bis(3-diethylaminopropyl)xanthene-2,7-dimethanol.

EXAMPLE 38

Following the procedure of Example 37, only substituting for 2,7-bis(4-diethylaminobutyryl)xanthene an appropriate molar equivalent amount of 2,6-bis(3-diethylaminopropionyl)xanthene, 2,7-bis(5-dimethylaminopropionyl)xanthene, 4,6-bis(4-dibutylaminobutyryl)dibenzofuran or 2,8-bis(3-diethylaminopropionyl)dibenzofuran the following respective products are obtained:

α,α'-bis(2-diethylaminoethyl)xanthene-2,6-dimethanol,
α,α'-bis(4-dimethylaminobutyl)xanthene-2,7-dimethanol,
α,α'-bis(3-dibutylaminopropyl)dibenzofuran-4,6-dimethanol,
and α,α'-bis(2-diethylaminoethyl)dibenzofuran-2,8-dimethanol.

EXAMPLE 39

2,7-Bis(4-diethylamino-1-butenyl)xanthene

A solution of 16.3 g (0.035 mole) of α,α'-bis(3-diethylaminopropyl)xanthene-2,7-dimethanol is dissolved in a mixture of 25 ml of ethylene glycol monoethyl ether and 25 ml of concentrated hydrochloric acid and heated on the steam bath for 5 minutes. The solution is diluted with an equal volume of water and made alkaline with a 20% sodium hydroxide solution. The resulting solution is extracted with ether, and the extracts are combined, washed with water, and a saturated sodium chloride solution, dried over anhydrous magnesium sulfate, filtered and evaporated to dryness in vacuo. The residue is recrystallized twice from ethanol and twice from isopropanol to give 2,7-bis(4-diethylamino-1-butenyl)xanthene.

EXAMPLE 40

Following the procedure of Example 39, only substituting for α,α'-bis(3-diethylaminopropyl)xanthene-2,7-dimethanol, an appropriate molar equivalent amount of the respective products of Example 38, the following compounds are obtained:

2,6-bis(3-diethylamino-1-propenyl)xanthene,
2,7-bis(5-dimethylamino-1-pentenyl)xanthene,
4,6-bis(4-dibutylamino-1-butenyl)dibenzofuran,
and 2,8-bis(3-diethylamino-1-propenyl)dibenzofuran.

The following Examples 41 to 44 are illustrative of pharmaceutical compositions, containing as active ingredients, compounds of general Formula 1.

EXAMPLE 41

An illustrative composition for tablets is as follows:

|  | Per Tablet |
|---|---|
| (a) 2,7-bis(2-dimethylaminoacetyl)-xanthene dihydrochloride | 100.0 mg |
| (b) wheat starch | 15.0 mg |
| (c) lactose | 33.5 mg |
| (d) magnesium stearate | 1.5 mg |

A portion of the wheat starch is used to make a granulated starch paste which together with the remainder of the wheat starch and the lactose is granulated, screened and mixed with the active ingredient, that is, (a), and the magnesium stearate. The mixture is compressed into tablets weighing 150 mg each.

EXAMPLE 42

An illustrative composition for a parenteral injection is the following wherein the quantities are on a weight to volume bases.

|  | Amount |
|---|---|
| (a) 3,6-bis(2-diethylaminoethylthio)-xanthen-9-one dihydrochloride | 100.0 mg |
| (b) sodium chloride | q.s. |
| (c) water for injection to make | 10.0 ml |

The composition is prepared by dissolving the active ingredient, that is (a), and sufficient sodium chloride in water for injection to render the solution isotonic. The composition may be dispensed in a single ampule containing 100 mg of the active ingredient for multiple dosage or in 10 ampules for single dosage.

EXAMPLE 43

An illustrative composition for hard gelatin capsules is as follows:

|  | Per Capsule |
|---|---|
| (a) 2,8-bis(2-diethylaminoethoxy)-dibenzofuran dihydrochloride | 200.0 mg |
| (b) talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 44

An illustrative composition for pills is as follows:

|  | Per Pill |
|---|---|
| (a) bis(3-diethylaminopropyl)dibenzofuran-2,8-dicarboxylate dihydrochloride | 200 mg |
| (b) corn starch | 130 mg |

23

-continued (c) liquid glucose     20 ml

The pills are prepared by blending the active ingredient (a) and the corn starch then adding the liquid glucose with thorough kneading to form a plastic mass from which the pills are cut and formed.

EXAMPLE 45

2,7-Bis(5-diallylaminovaleryl)xanthene

A mixture of 41.9 g (0.1 mole) of 2,7-bis(5-chlorovaleryl)xanthene, 2 g of potassium iodide, 100 ml of diallylamine and 200 ml of tetrahydrofuran is heated and stirred at 120°C for 24 hours. After cooling, the reaction mixture is filtered and the filtrate evaporated to dryness. The resulting residue is cooled, dissolved in 10% HCl, extracted with diethyl ether and made alkaline. The product is extracted with methylene chloride, evaporated to dryness, recrystallized six times from heptane and dried in vacuo to give 2,7-bis(5-diallylaminovaleryl)xanthene. M.P. 54°–55°C.

EXAMPLE 46

Bis(3-diallylaminopropyl)dibenzofuran-2,8-dicarboxylate dihydrochloride

A solution of 8.8 g (0.03 mole) of dibenzofuran-2,8-dicarbonyl chloride and 9.3 g (0.06 mole) of 3-diallylaminopropanol in 400 ml of chloroform is refluxed for 16 hours. On cooling, petroleum ether is added to precipitate the product which is recrystallized from methanolbutanone to give bis(3-diallylaminopropyl)-dibenzofuran-2,8-dicarboxylate dihydrochloride. M.P. 223°–225°C.

EXAMPLE 47

2,7-Bis(3-diethylaminopropionyl)xanthene dihydrochloride hydrate

A mixture of 18.2 g (0.05 mole) of 2,7-bis(3-chloropropionyl)xanthene, 2 g of potassium iodide, 100 ml of diethylamine and 100 ml of tetrahydrofuran is allowed to stand for 3 days then filtered. The filtrate is evaporated to dryness leaving a residue which is treated with 10% HCl and filtered. The filtrate is made alkaline, extracted with methylene chloride and treated with ethereal HCl. The resulting precipitate is filtered, recrystallized from methanol-diethyl ether and hydrated in a constant humidity chamber to give 2,7-bis(3-diethylaminopropionyl)xanthene dihydrochloride hydrate. M.P. 184.5°–185.5°C.

I claim:

1. A method of treating conditions of delayed hypersensitivity which comprises administering to a patient in need thereof a compound selected from the formula

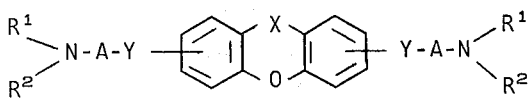

wherein X is selected from a bond, —CH$_2$—, or carbonyl; each Y is selected from a vinylene group,

carbonyl, oxygen, divalent sulfur, or carbonyloxy, with the proviso that when Y is a vinylene group or

X is other than carbonyl; A is selected from a straight or branched alkylene chain of from 1 to 6 carbon atoms with the proviso that when Y is a vinylene group A contains from 1 to 5 carbon atoms, and with the proviso that when Y is a carbonyloxy, A contains from 2 to 6 carbon atoms; each of $R^1$ and $R^2$ is selected from hydrogen, straight or branched lower alkyl of from 1 to 4 carbon atoms, or alkenyl of from 3 to 6 carbon atoms having the vinyl unsaturation in other than the 1-position; and pharmaceutically acceptable acid addition salt thereof, in an amount effective to suppress delayed hypersensitivity.

2. A method of claim 1 wherein each of $R^1$ and $R^2$ is straight or branched lower alkyl of from 1 to 4 carbon atoms.

3. A method of claim 2 wherein each Y is a vinylene group.

4. A method of claim 2 wherein each Y is

5. A method of claim 2 wherein each Y is carbonyl.
6. A method of claim 2 wherein each Y is oxygen.
7. A method of claim 2 wherein each Y is divalent sulfur.
8. A method of claim 2 wherein each Y is carbonyloxy.
9. A method of claim 5 wherein the compound is 2,7-bis(2-dimethylaminoacetyl)xanthene or a pharmaceutically acceptable acid addition salt thereof.

* * * * *